US006913878B2

(12) United States Patent  (10) Patent No.: US 6,913,878 B2
Nakamura et al.  (45) Date of Patent: Jul. 5, 2005

(54) METHOD OF DETECTING DNA SINGLE STRAND BREAKS

(75) Inventors: Jun Nakamura, Chapel Hill, NC (US); James A. Swenberg, Pittsboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 10/337,012

(22) Filed: Jan. 6, 2003

(65) Prior Publication Data

US 2004/0132004 A1 Jul. 8, 2004

(51) Int. Cl.[7] .......................... C12Q 1/68; C12N 15/85; C12N 15/09; G01N 33/53; C12P 19/24
(52) U.S. Cl. ........................ 435/4; 435/6; 435/7.2; 435/25; 435/29; 435/42; 435/94; 435/455; 435/30; 435/325; 436/210
(58) Field of Search ........................ 435/6, 455, 7.2, 435/94, 29, 30, 4, 42, 25

(56) References Cited

U.S. PATENT DOCUMENTS 5,185,450 A  2/1993 Owen
6,063,587 A  5/2000 Ishiyama et al.

OTHER PUBLICATIONS

Cell Proliferation Kit II (XTT), Oct. 1999;available at roche–applied–science.com/cfm/country_id_a.jsp.*
Berridge and Tan. Protoplasm, 1998; 205:74–82.*
Lin et al. Carcinogenesis, 2001; 22(4):627–34.*
Cell Proliferation Reagent WST–1, Nov. 2002, available at roche–applied–science.com/cfm/country_id_a.jsp.*
Cell Proliferation Reagent Kit I (MTT), Jul. 2002, available at roche–applied–science.com/cfm/country_id_a.jsp.*

Berridge et al.; "The Biochemical and Cellular Basis of Cell Proliferation Assays That Use Tetrazolium Salts" *Biochemica* 4, 14–19 (1996).
Berridge et al.; "Trans–plasma membrane electron transport: a cellular assay for NADH– and NADPH–oxidase based on extracellular, superoxide–mediated reduction of the sulfonated tetrazolium salt WST–1" *Protoplasma* 205 74–82 (1998).
Krokart et al; "DNA glycosylases in the base excision repair of DNA" *Biochem. J.* 325 1–16 (1997).
Vodenicharov et al.: "Base excision repair is efficient in cells lacking poly(ADP–ribose) polymerase 1" *Nucleic Acids Research* 28:20 3887–3896 (2000).
International Search Report for PCT US04/00068; date of mailing Oct. 29, 2004.
Boehringer Mannheim, *Apoptosis and Cell Proliferation, Biochemica*, 2nd Ed., pp. 70–72 (1998).
Ishiyama, Munetaka, *Topics on Chemistry: Why is the water–soluble formazan necessary?*, Bojinda Newsletter, vol. 2, 15 pages (2002).
Technical Manual, *Cell Proliferation Assay and Cytotoxicity Assay: Cell Counting Kit–8* (Sep. 18, 2002).

* cited by examiner

*Primary Examiner*—Gerry Leffers
*Assistant Examiner*—Ramin Akhavan
(74) *Attorney, Agent, or Firm*—Myers Bigel Sibley & Sajovec, P.A.

(57) ABSTRACT

A method of detecting increased levels of DNA single strand breaks in a eukaryotic cell sample, comprising the steps of: (a) contacting a eukaryotic cell sample to a water-soluble tetrazolium salt under conditions in which said tetrazolium salt is converted to a formazan dye in said cell sample in the presence of NADH or NADPH; and then (b) detecting the presence of the formazan dye in said cell sample, with decreased levels of the formazan dye indicating increased levels of DNA single strand breaks in the eukaryotic cell sample.

24 Claims, 6 Drawing Sheets

METHOD OF DETECTING DNA SINGLE STRAND BREAKS

This invention was made in the course of research sponsored by the National Institute of Environmental Health Sciences (NIEHS Grant Nos. P30-ES10126, R42-ES11746-02, and P42-ES05948). The U.S. government has certain rights in this invention.

FIELD OF THE INVENTION

This invention relates to methods for the rapid detection of single strand breaks in DNA.

BACKGROUND OF THE INVENTION

Cellular DNA is continuously exposed to insults from exposure to endogenous and exogenous alkylating agents and oxidative stress. Base excision repair appears to be primarily responsible for the elimination of most of these deleterious DNA lesions (Wood (1996) *Annu. Rev. Biochem.* 65:135–167). In addition to DNA lesions induced by these agents, spontaneous depurination/depyrimidination could introduce a significant amount of apurinic/apyrimidinic (AP) sites under physiological conditions (Nakamura, et al. (1998) *Cancer Res.* 58:222–225). Using a combination of an aldehyde reactive probe and slot blot technique, the spontaneous depurination rate under physiological conditions was found to be 1.5 AP sites per $10^6$ nucleotides per day, which corresponds to 9000 AP sites per cell per day (Nakamura, et al. (1998) *Cancer Res.* 58:222–225). Modified bases and AP sites introduce DNA single strand breaks as intermediates of base excision repair pathway (Krokan, et al. (1997) *Biochem. J.* 325:1–16). In this process, a DNA glycosylase cleaves the N-glycosylic bond between modified or even normal bases and deoxyriboses, leaving AP sites (Krokan, et al. (1997) *Biochem. J.* 325:1–16; Lindahl (2000) *Mutat. Res.* 462:129–135). The AP sites generated by the DNA glycosylase are subsequently incised by a class II AP endonuclease (Demple and Harrison (1994) *Annu. Rev. Biochem.* 63:915–948), resulting in a 3'-hydroxyl group and a 5'-deoxyribosephosphate (5'-dRp). After excision of 5'-dRp by DNA polymerase β (β-pol), repair is completed by the polymerase and ligase activities of β-pol and DNA Ligase, respectively. Furthermore, reactive oxygen species (ROS) also induce lesions by hydrogen abstraction of the deoxyribose, frequently producing oxidized AP sites as well as DNA single strand breaks (Breen and Murphy (1995) *Free Radic. Biol. Med.* 18:1033–1077). In B-form duplex DNA, hydrogen atoms at the C-4' and C-5' positions of deoxyribose are the most accessible to ROS (Von Sonntag (1987) In: The Chemical Basis of Radiation Biology, pp. 238–249, Taylor and Francis, London), leading to 3'- and 5'-terminal lesions, respectively. Therefore, DNA single strand breaks are one of the most frequent DNA lesions in mammalian cells even under physiological conditions. Single cell agarose gel electrophoresis, i.e., the Comet assay, is a well-known and sensitive assay to assess the amount of single strand breaks and their repair (Tice, et al. (2000) *Environ. Mol. Mutagen.* 35:206–221). However, this assay usually requires alkaline conditions to denature DNA for subsequent gel electrophoresis. Alkylating agents and oxidants introduce either alkaline-labile base lesions or AP sites leading to single strand breaks under basic conditions (Burrows and Muller (1998) *Chem. Rev.* 98:1109–1152; Miyamae, et al. (1997) *Mutat. Res.* 393:107–113). Artifactual formation of single strand breaks may therefore be introduced during DNA extraction. Therefore, it is difficult to accurately determine the number of single strand breaks and an imbalance in their repair using isolated cellular DNA.

SUMMARY OF THE INVENTION

Figure 1:
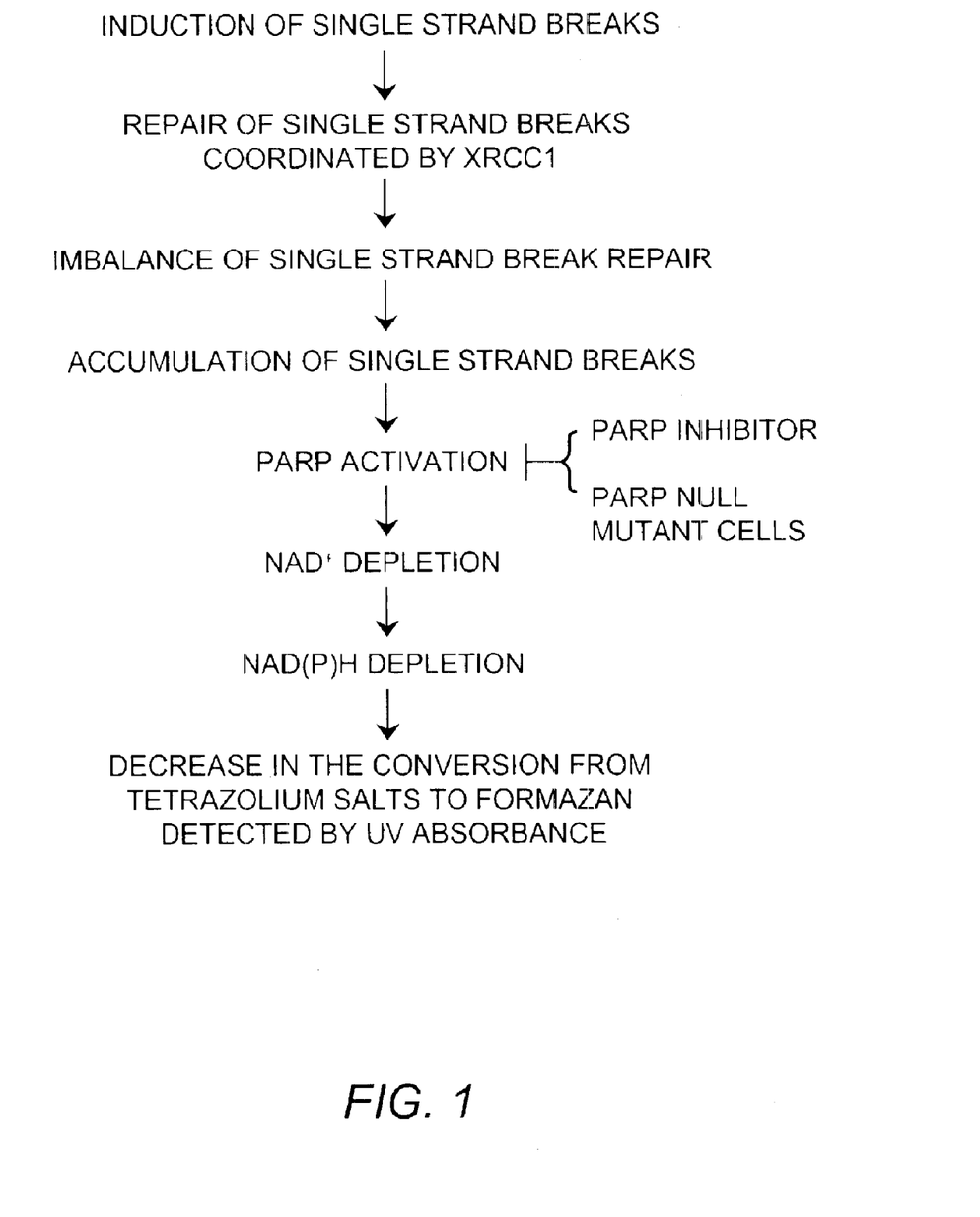
FIG. 1 depicts an imbalance of single strand break repair and $NAD^+$ and NAD(P)H depletion.

In general, a sensitive, reliable, real-time method of detecting an imbalance of DNA single strand break repair has now been found which indirectly measures poly(ADP-ribose) polymerase (PARP) activation through the depletion of intracellular NADH and NADPH (FIG. 1). This invention is explained in greater detail below.

The present invention provides a method of detecting increased levels of DNA single strand breaks in a cell or cell sample. The method comprises the steps of: (a) contacting a cell to a water-soluble tetrazolium salt under conditions in which the tetrazolium salt is converted to a formazan dye in the cell in the presence of NADH or NADPH; and then (b) detecting the presence of the formazan dye in the cell, with decreased levels of the formazan dye indicating increased levels of DNA single strand breaks in the cell (e.g., "decreased" relative to any suitable standard, such as a formazan dye produced in a standard or control cell under the same contacting and detecting conditions). The formazan dye may be water soluble or water insoluble, although the use of water-insoluble formazan dyes necessitates the lysis of the cells prior to the detecting step. In particular embodiments, the cell is a live cell, or culture or sample of live cells. The contacting step is preferably carried out in an aqueous solution, and the detecting step may be carried out by any suitable means, such as by detecting UV absorbance (to be treated as the same as detecting UV transmission herein).

In one embodiment, a test compound is contacted to the cell before or during the contacting step, with increased levels of single stranded breaks indicating the test compound is genotoxic to the cell, and reduced levels of single stranded breaks indicating the test compound is protective to the cell. The cell may be subjected to oxidative stress before or during the contacting step, and a test compound is contacted to the cell before or during the contacting step, with increased levels of single stranded breaks indicating the test compound exacerbates the oxidative stress, and reduced levels of single stranded breaks indicating the test compound is protective against the oxidative stress.

In another embodiment, where the cell is collected from a plant or animal subject and contacted to a genotoxic compound, the amount of DNA single strand breaks in the cell is compared to that of a like cell which has not been contacted to the genotoxic compound, to determine the susceptibility of that subject to the genotoxic compound.

In still another embodiment where the cell is collected from a plant or animal subject and subjected to oxidative stress, the amount of DNA single strand breaks in the cell is compared to that of a like cell which has not been subjected to the oxidative stress, to determine the susceptibility of that subject to oxidative stress.

The foregoing and other objects and aspects of the present invention are explained in detail in the specification set forth below.

DETAILED DESCRIPTION OF PREFERRED EMBODIMENTS

"Alkyl" as used herein typically refers to loweralkyl or C1–C4 alkyl, including but not limited to methyl, ethyl, propyl, and butyl.

"Alkoxy" as used herein typically refers to loweralkoxy or C1–C4 alkoxy, including but not limited to methyl, ethyl, propyl, and butyl.

"Alkali metals" as used herein include but are not limited to sodium and potassium, with sodium being preferred.

"Halogen" as used herein may be any suitable halogen atom, including but not limited to fluoro, bromo, chloro and iodo.

"Cell" or "cells" as used herein refer to any type of cell, preferably eukaryotic cells including plant and animal cells. Suitable cells include yeast cells and mammalian cells (e.g., dog, cat, rabbit, mouse, rat, human). The cell may be of any tissue type, including but not limited to skin, blood, etc.

"Oxidative stress" as used herein refers to any type of oxidative stress, including but not limited to exposure to ionizing radiation, compounds that generate free radicals in the cells, etc.

"Genotoxic" as used herein refers to compounds that are toxic due to disruption or breakage of nucleic acids within a cell, and is intended to include, for example, carcinogenic and teratogenic compounds.

Applicants specifically intend that the disclosures of all United States patent references cited herein be incorporated by reference herein in their entirety.

Water-soluble tetrazolium salts which generate both water-insoluble or water-soluble formazan dyes are known and described in, for Example, U.S. Pat. No. 6,063,587 to Ishiyama et al; U.S. Pat. No. 5,185,450 to Owen; D. A. Scudiero, R. H. Shoemaker, K. D. Paull, A. Monks, S. Tierney, T. H. Nofziger, M. J. Curens, D. Seniff, M. R. Boyd, Evaluation of a Soluble Tetrazolium/Formazan Assay for Cell Growth and Drug Sensitivity in Culture Using Human and Tumor Cell Lines, Cancer Res. 48, 4827(1988); N. W. Roehm, G. H. Rodgers, S. M. Hatfield, A. L. Glasebrook, An Improved Colorimetric Assay for Cell Proliferation and Viability Utilizing the Tetrazolium Salt XTT, J. Immunol. Methods, 142, 257(1991); M. G. Stevens, S. C. Olsen, Comparative Analysis of Using MTT and XTT in Colorimetric Assays for Quantitating Bovine Neutrophil Bactericidal Activity, J. Immunol. Methods, 157, 225(1993).

In one embodiment as disclosed in U.S. Pat. No. 6,063, 587 to Ishiyama et al., such tetrazolium salts are sulfonated tetrazolium salts, such as compounds of the general formula:

wherein A, B and C are independently selected aryl or heteroaryl groups (e.g., phenyl), which may be substituted or unsubstituted (e.g., one or two times with independently selected groups such as alkyl, alkoxy, halo, nitro, cyano, carboxy, etc.) with at least one of A, B, and C being substituted at least once (and preferably twice) with $SO_3^-$.

In some embodiments, the tetrazolium salt has the general formula:

wherein $R^1$ and $R^2$ independently represent hydrogen or nitro, and M represents an alkali metal or an ammonium.

In other embodiments, the water-soluble tetrazolium salt has the general formula:

wherein $R^1$ and $R^2$ independently represent a hydrogen atom, nitro group, cyano group, carboxyl group, or a halogen atom; $R^3$ represents an alkyl group or an alkoxyl group; and M represents an alkali metal or an ammonium.

Other examples of water-soluble tetrazolium salts are tetrazolium compounds having attached as a side chain to the tetrazolium ring a naphthalene ring having two sulfonate groups thereon (such as 2-naphthyl-6,8disulfonate), or tetrazolium compounds having attached to the tetrazolium ring side chains having one sulfonate group and one group which is less acidic than the stilfonate group selected from the group consisting of oxyacetic acid group or phosphomonoester group, rendering the compound and the related formazan water soluble, as described in U.S. Pat. No. 5,185,450 to Owen.

In one embodiment, the water-soluble tetrazolium salt is WST-8, or 2-(2-methoxyl-4-nitrophenyl)-3-(4-nitrophenyl)-5-(2,4-disulfophenyl)-2H-tetrazolium, monosodium salt.

In another embodiment, the water soluble tetrazolium salt is WST-1, or 4-[3-(4-iodophenyl)-2-(4-nitrophenyl)-2H-5-tetrazolio]1,3-benzene disulfonate.

In another embodiment, the water soluble tetrazolium salt is XTT, or 2,3-bis[2-methyoxy-4-nitro-5-sulfophenyl]-2H-tetrazolium-5-carboxanilide (also called "(2,3-bis[2-methoxy-4-nitro-5-sulfophenyl]-2H-tetrazolium-5-carboxyanilide inner salt").

In another embodiment, the water-soluble tetrazolium salt is MTS, or 3-(4,5-dimethylthiazol-2-yl)-5-(3-carboxynethoxyphenyl)-2-(4-sulfophenyl)-2H-tetrazolium, inner salt.

In another embodiment, the water-soluble tetrazolium salt is MTT, or 3-[4,5-dimethylthiazol-2yl]2,5-diphenyltetrazolium bromide (although MTT produces a water-insoluble dye, it may be used by lysing the cells prior to the detecting or determining step).

In still other embodiments, the water soluble tetrazolium salt is WST-3, or 2-(4-Iodophenyl)-3-(2,4-dinitrophenyl)-5-(2,4-disulfophenyl)-2H-tetrazolium, sodium salt; WST-4, or 2-Benzothiazolyl-3-(4-carboxy-2-methoxyphenyl)-5-[4-(2-sulfoethyl-carbamoyl)phenyl]-2H-tetrazolium; or WST-5, or 2,2'-Dibenzothiazolyl-5,5'-bis[4-di(2-sulfoethyl) carbamoylphenyl]-3,3'-(3,3'-dimethoxy-4,4'-biphenylene) ditetrazolium, disodium salt.

DNA single strand breaks are one of the most frequent lesions in genomic DNA generated by either oxidative stress or by base excision repair pathways. DNA single strand breaks induce activation of PARP-1 (Lautier, et al. (1993) *Mol. Cell Biochem.* 122:171–193; de Murcia, et al. (1994) *Mol. Cell Biochem.* 138:15–24) which depletes intracellular $NAD^+$ (Berger (1985) *Radiat. Res.* 101:4–15). A decrease in the intracellular $NAD^+$ further depletes ATP as well as NADH and NADPH (Carson, et al. (1986) *Exp. Cell Res.* 164:273–281; Oleinick and Evans (1985) *Radiat. Res.* 101:29–46). Accordingly, The present invention provides a method of detecting DNA single strand breaks in a cell by measuring the intracellular levels of NADH and NADPH, herein referred to as NAD(P)H.

In one embodiment, a method of the invention is carried out by obtaining a sample, such as a biopsy sample, tissue, cell or fluid (e.g., whole blood or plasma), from a subject; contacting the sample with a water-soluble tetrazolium salt and measuring the levels of NAD(P)H in the sample via the reduction of the tetrazolium salt to a formazan dye. The formation of the formazan dye may be measured by any suitable technique such as by using any standard spectrophotometer. Preferably, the spectrophotometer can read a plurality of samples simultaneously (e.g., a 96-well plate reader). Levels of NAD(P)H in a sample may be compared to a control or monitored over a period of time (e.g., 30 minutes to 4 or 8 hours) to assess whether there is an imbalance in DNA single strand break repair mechanisms. A sample with reduced levels of NAD(P)H is indicative of PARP activation and hence DNA single strand breaks in the subject from which the sample was obtained. Accordingly, a method of detecting DNA single strand breaks may be used as part of a screen in subjects suspected of having been exposed to a DNA damaging agent. Moreover, the detection method of the invention may be used alone or in combination with other well-known diagnostic methods to confirm DNA single strand breaks.

Single strand breaks in DNA may have a genetic- or age-related basis or may result from exposure to agents including those which generate DNA adducts by alkylation (e.g., methylmethane sulfonate (MMS), ethylmethane sulfonate (EMS), N-methyl-N-nitro-N-nitrosoguanine (MNNG), dimethylnitrosamine (DMN), dimethyl sulfate); reactive oxygen species (e.g., peroxides); base analogs, such as bromouracil, 5-hydroxymethyl-2'-deoxyuridine, and aminopurine; or radiation such as ultraviolet and ionizing radiation (e.g., X- and gamma-rays).

Detection of DNA single strand breaks in a cell as determined by measuring the intracellular levels of NAD (P)H is also useful for monitoring therapeutic effects during clinical trials and other treatment. Thus, the therapeutic effectiveness of an agent, such as a radionucleide for radiation therapy or a cytotoxic agent for chemotherapy, designed to cause DNA single strand breaks in a cell, may be monitored using the activation of PARP, i.e, reduction in NAD(P)H, as an end-point target.

Moreover, a detection method of the invention may be used to screen for individuals with a diminished capacity for either the repair of single strand breaks or base excision repair.

A further aspect of the invention provides a method of detecting a DNA damaging agent in a sample. A sample may be either of biological or environmental origin. Biological samples include those provided above as well as food products and ingredients such as dairy items, vegetables, meat and meat by-products, and waste. Environmental samples include environmental material such as surface matter, soil, water, wastewater, sewage, sludge, industrial samples (e.g., industrial water), as well as samples obtained from food and dairy processing instruments, apparatus, equipment, disposable and non-disposable items. In addition to these environmental samples, it is contemplated that drinking water may be used with the method of the present invention. It is intended that the term drinking water encompass all types of water used for consumption by humans and other animals, including but not limited to well water, run-off water, water stored in reservoirs, rivers, streams, etc. The method provides contacting a test cell with a sample suspected of having a DNA damaging agent, allowing the test cell to incubate in the presence of the sample, and detecting whether DNA single strand breaks have occurred in the test cell by measuring the levels of NAD(P)H in said cell. In addition, base excision repair-deficient cell lines such as XRCC1-deficient cells, AP endonuclease-deficient cells, DNA glycosylase-deficient cells, DNA ligase-deficient cells or DNA polymerase null mutant cells may be exposed to the DNA damaging agent to determine whether the DNA damage induced by said agent is repaired by base excision repair. Methods for detecting DNA single strand breaks in a cell by measuring the intracellular levels of NAD(P)H in a cell are provided herein. In addition, since the process of DNA repair mostly requires DNA synthesis, this cell-based method combined with DNA synthesis inhibitor, such as hydroxynrea, enhance accumulation of DNA SSBs induced by DNA damaging agents. Therefore, this application enables researchers to sensitively and conveniently detect DNA damaging agents using ordinary DNA repair-proficient cells.

A further aspect of the invention provides a cell-based method of identifying agents that modulate the activation of DNA repair enzymes. In an unperturbed cell, DNA repair enzymes, such as PARP, are in an inactive state. Upon DNA single strand breaks, these enzymes are activated and in the case of PARP cause a concurrent reduction in NAD(P)H. Therefore, an agent which modulates the activation of PARP may be identified in a screening assay by contacting a cell with an agent and measuring the intracellular levels of NAD(P)H. The assay may further comprise a washing step prior to the addition of the tetrazolium salt to remove residual agent which may interact with the tetrazolium salt. PARP activation may be modulated by blocking, inhibiting or decreasing activation as well as stimulating, enhancing, or increasing the rate or amount of activation. A typical screening assay for inhibitors comprises contacting an unperturbed cell with an agent and a genotoxicant such as methyl methanesulfonate, and determining whether said agent blocks or inhibits activation of PARP by measuring the intracellular levels of NAD(P)H. Agents which inhibit PARP activation are useful as radiosensitizers or chemosensitizers in the treatment of a wide variety of human tumors. A typical screening assay for enhancers of PARP activation comprises contacting an unperturbed cell with an agent and determining whether said agent enhances or stimulates activation of PARP by measuring the intracellular levels of NAD(P)H. Agents which enhance or stimulate the activation of PARP are useful as chemotherapeutic agents against cancer cells. Methods for measuring the intracellular levels of NAD(P)H in a cell are provided herein.

A further aspect of the invention provides a cell-based method of identifying DNA synthesis inhibitors not only for cancer chemotheraputic agents but also for anti-HIV drugs. As described earlier, a majority of DNA repair pathway require DNA synthesis after excision of damaged bases or nucleotides. Therefore, a combination of DNA damaging agents and this cell-based assay can efficiently screen chemicals or proteins which interfere DNA synthesis within 4 hours. Since DNA synthesis inhibitor is known to be useful as anti-HIV agents, this method can be applied to HIV-related research.

Agents which may be screened using the screening assays provided herein encompass numerous chemical classes, though typically they are organic molecules, preferably small organic compounds having a molecular weight of more than 100 and less than about 2,500 daltons. Agents comprise functional groups necessary for structural interaction with proteins, particularly hydrogen bonding, and typically include at least an amine, carbonyl, hydroxyl or carboxyl group, preferably at least two of the functional chemical groups. The agents often comprise cyclical carbon or heterocyclic structures and/or aromatic or polyaromatic structures substituted with one or more of the above functional groups. Agents may also be found among biomolecules including peptides, antibodies, saccharides, fatty acids, steroids, purines, pyrimidines, derivatives, structural analogs or combinations thereof. Such agents may be obtained from a wide variety of sources including libraries or combinatorial libraries of synthetic or natural compounds.

A variety of other reagents may be included in the screening assays. These include reagents like salts, neutral proteins, e.g., albumin, detergents, etc. which may be used to facilitate optimal protein-protein binding and/or reduce non-specific or background interactions. Also, reagents that otherwise improve the efficiency of the assay, such as protease inhibitors, nuclease inhibitors, anti-microbial agents, and the like may be used. The mixture of components may be added in any order that provides for the requisite binding.

A further aspect of the invention provides a kit to detect a DNA damaging agent in a sample. The kit comprises a tetrazolium salt. The kit may further comprise a test cell. Further provided in the kit may be a means for comparing the amount of NAD(P)H present with a standard. The kit may be packaged in a suitable container and further comprise instructions, such as printed instructions, for using the kit to detect DNA damaging agents, such as instructions for carrying out the methods described.

In one embodiment, the detecting step is followed by the step of: (c) generating a quantitative indication of the amount of DNA single strand breaks in the cell from the detected presence of formazan dye. This generating step may be carried out by any suitable technique, such as by comparing the levels of the formazan dye detected in the selected cell or cells against that in a control cell, by determining the amount of formazan dye formed over time, by comparing against another known standard, or any other suitable technique.

The present method may be performed in a real-time manner, i.e., a sample of living cells may be monitored continuously without performing an extraction step, and with live cells, and with multiple measures being taken from the same cell or cell sample over time. Furthermore, fewer than 500,000 cells, fewer than 200,000 cells, fewer than 100,000 cells, fewer than 10,000 cells, and even fewer than 1,000 cells (depending upon the sensitivity of the equipment) are required for the assay. Finally the steps of the assay may be carried out rapidly, for example in not more than 4, 3, 2 or even one hour, as compared to the lengthy times required for currently available techniques.

The examples, which follow, are set forth to illustrate the present invention, and are not to be construed as limiting thereof.

EXAMPLE 1

Cell Culture

XRCC1-proficient and -deficient CHO cells (Taylor, et al. (2002) *Mol. Cell. Biol.* 22:2556–2563) were cultured as monolayers in alpha-minimal essential medium (INVITROGEN™, Carlsbad, Calif.) supplemented with 10% fetal bovine serum (Sigma-Aldrich, St. Louis, Mo.), 100 µg/mL penicillin, and 100 µg/mL streptomycin. Immortalized mouse embryonic fibroblasts derived from PART-$1^{+/+}$ and PARP-$1^{-/-}$ were maintained in Dulbecco's modified Eagle's medium, 4.5 g/Liter glucose medium (INVITROGEN™, Carlsbad, Calif.) supplemented with 10% fetal bovine serum and 0.5% gentamicin (Schreiber, et al. (2002) *J. Biol. Chem.* 277:23028–23036). Human lymphoblastoid cells (GM15030, GM15061, GM15237, GM15268, GM15339, GM15349, GM15365, and GM15380; Coriell Cell Repositories, Camden, N.J.) were grown in RPMI 1640 medium (INVITROGEN™, Carlsbad, Calif.) supplemented with 15% fetal bovine serum (Sigma-Aldrich, St. Louis, Mo.), 100 µg/mL penicillin, and 100 µg/mL streptomycin. The cells were maintained in a humidified atmosphere of 5% $CO_2$ and 95% air at 37° C.

EXAMPLE 2

Detection of Intracellular NAD(P)H

A water-soluble tetrazolium salt was used to measure the amount of intracellular NAD(P)H through the reduction to a formazan dye. The total amount of NAD(P)H within viable cells in the medium was determined periodically by a spectrophotometer. Cells were seeded into 96-well plates (CHO cells and mouse fibroblasts: $5 \times 10^3$ cells/well; lymphoblastoid cells: $15 \times 10^3$ cells/well) and were cultured in 100 µL of medium with fetal bovine serum and antibiotics as described. After a 30-minute incubation, cells were treated with MMS at indicated concentrations and 1/10 volume of CCK-8 solution (Dojindo Molecular Technology, Gaithersburg, Md.) which consisted of a water-soluble 2-(2-methoxy-4-nitrophenyl)-3-(4-nitrophenyl)-5-(2,4-disulfophenyl)-2H-tetrazolium monosodium salt (WST-8; 5 mM) and 1-Methoxy-5-methylphenazinium methylsulfate (1-Methoxy PMS; 0.2 mM) as an electron mediator. Cells in each well were further cultured for up to 4 hours. WST-8 produced a water-soluble yellow-colored formazan dye through its bioreduction either in the presence of an electron carrier, such as 1-Methoxy PMS, Diaphorase, a flavoenzyme, or directly by NAD(P)H. Therefore, the reduction of tetrazolium salts predominantly depends on the amount of intracellular NAD(P)H. The amount of formazan dye produced by the living cells in the medium was determined approximately every 30 minutes by a spectrophotometer and compared to the values of the control. Absorbance was recorded in a 96-well plate reader at 450 nm with a 650 nm reference filter. A medium blank was prepared with only medium and CCK-8 reaction solution. Decreases in the intracellular NAD(P)H were assessed by comparing the absorbance of a well containing cells treated with MMS against that of a well with cells treated with phosphate-buffered saline (PBS) only.

Cell death was determined with trypan blue staining. Cells were treated with MMS at 0, 0.75, and 1.5 mM for 1 and 4 hours. After trypsinization, cells were stained using a standard trypan blue dye-exclusion assay.

Figure 2:
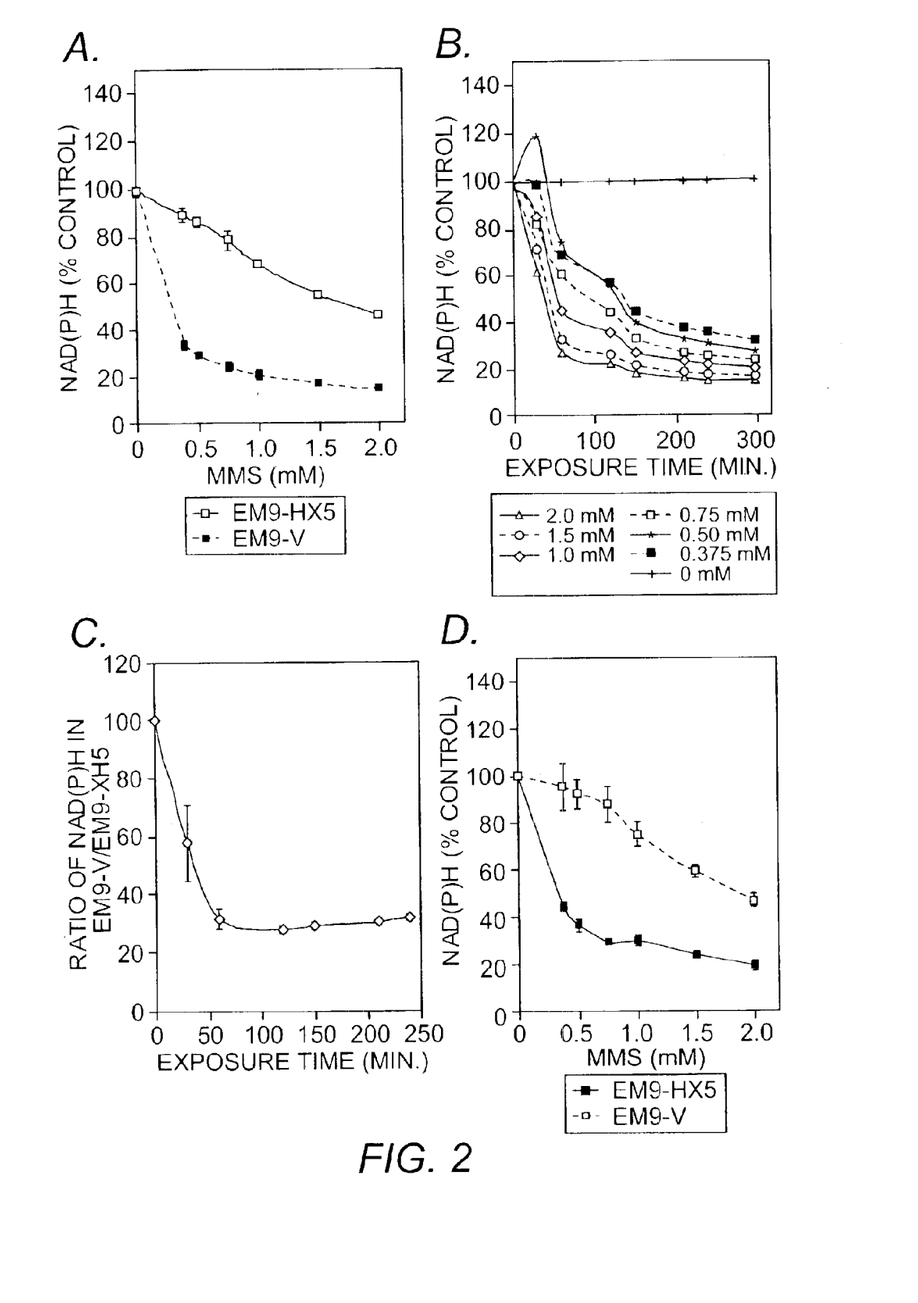
FIG. 2 shows the intracellular NAD(P)H level in living Chinese hamster ovary EM9 cells expressing empty vector (EM9-V) or human wild-type XRCC1 (EM9-XH5). Panel A shows NAD(P)H levels in cells exposed to methyl methanesulfonate (MMS) for 4 hours. Panel B shows the results of a real-time NAD(P)H assay of EM9-V cells exposed to MMS. Panel C is a time course of the ratio of NAD(P)H levels in EM9-V cells versus EM9-XH5 cells as a function of the exposure time with MMS. Panel D shows the reproducibility of the NAD(P)H assay as the mean of four independent experiments. Except for the data presented in Panel D, results were from triplicate samples and the reproducibility was confirmed at least three times; bars, standard deviation.

XRCC1 functions as a scaffold for interaction with other base excision repair-associated proteins including human AP endonuclease (APE1), DNA Pol-β, DNA Ligase III, Polynucleotide Kinase (PNK), and PARP-1 (Caldecott, et al. (1996) *Nucl. Acids Res.* 24:4387–4394; Whitehouse, et al. (2001) *Cell* 104:1–11; Kubota, et al. (1996) *EMBO J.* 15:6662–6670; Caldecott, et al. (1994) *Mol. Cell. Biol.* 14:68–76; Caldecott, et al. (1995) *Nucl. Acids Res.* 23:4836–4843) and is required for efficient single strand break repair and genetic stability in mammalian cells. Rodent cells lacking XRCC1 are hypersensitive to DNA damaging agents (Whitehouse, et al. (2001) *Cell* 104:1–11; Kubota, et al. (1996) *EMBO J.* 15:6662–6670; Caldecott, et al. (1994) *Mol. Cell. Biol.* 14:68–76). Loss of XRCC1 also results in decreased genetic stability, including increased frequencies of spontaneous and/or induced chromosome translocations and deletions (Caldecott, et al. (1995) supra; Carrano, et al. (1986) *Mutat. Res.* 162:233–239; Dominguez, et al. (1998) Mutat. Res. 398:67–73; Thompson, et al. (1982) *Mutat. Res.* 95:427–440; Veld, et al. (1998) *Mutat. Res.* 398:83–92; Zdzienicka, et al. (1992) *Mutagenesis* 7:265–269). Using water-soluble tetrazolium salt to monitor the amount of intracellular NAD(P)H levels, isogenic CHO cell lines either proficient or deficient in XRCC1 were exposed to MMS. The cell lines used were XRCC1-deficient CHO EM9 cells expressing an empty pcD2E vector (EM9-V) as a single strand break repair-deficient cell and expressing wild-type human XRCC1 (pcD2EXH) (EM9-XH5) as a single strand break repair proficient cell (Whitehouse, et al. (2001) *Cell* 104:1–11). These cells were exposed to MMS at different concentrations for 4 hours. While the trypan blue exclusion assay demonstrated no major cell death during MMS treatment at any concentration, the intracellular NAD(P)H in both cell lines was significantly reduced by treatment with MMS in a dose-dependent manner (FIG. 2, Panel A). These data indicated the decrement of NAD(P)H was not due to a reduction in the number of viable cells.

To monitor the early events in the reduction of intracellular NAD(P)H, measurements were taken approximately every 30 minutes for the 4 hours of MMS exposure. Since CCK-8 does not require cell lysis for the determination of NAD(P)H, a real-time NAD(P)H assay was performed using a 96-well plate reader. The reduction of NAD(P)H was detected as early as 30 minutes during MMS exposure in EM9-V cells (FIG. 2, Panel B). Plotting the ratio of NAD (P)H in EM9-V versus EM9-XH5 cells as a function of the exposure time with MMS indicated that the ratio reached a plateau within 1 hour (FIG. 2, Panel C). Therefore, subsequent NAD(P)H measurements were performed on cells exposed to MMS for 1 to 4 hours. The reproducibility of the method provided herein is shown in FIG. 2, Panel D; four independent experiments were performed with 4 hour exposures of cells to MMS.

EXAMPLE 3

NAD(P)H Reduction in the Presence of PARP Inhibitors

Figure 3:
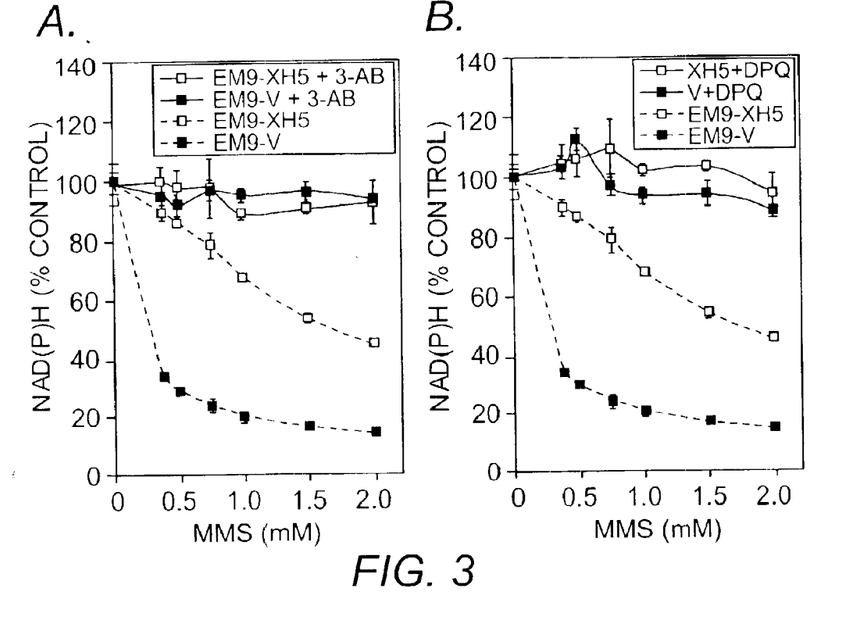
FIG. 3 shows the dose-dependency of the depletion of NAD(P)H in EM9-V and EM9-XH5 exposed to MMS for 4 hours in the absence or presence of PARP inhibitor, 3-aminobenzamide (3-AB) (10 mM; Panel A) or 3,4-dihydro-5-[4-(1-piperidinyl)butoxy]-1(2H)-isoquinolinone (DPQ) (90 µM; Panel B). Results represent triplicate samples and the reproducibility was confirmed at least three times. Bars, standard deviation.

PARP transfers hundreds of branched chains of ADP-ribose to a variety of nuclear proteins through its activation by DNA single strand breaks (Kubota, et al. (1996) supra; Caldecott, et al. (1994) supra). Under massive DNA damage, activation of PARP depletes its substrate, $NAD^+$ (Taylor, et al. (2002) supra). Since NAD(P)H are generated from NAD (P) by the reaction of dehydrogenase and its substrate, the decrease in the amount of NAD(P)H depletes NAD$^+$. To determine whether the reduction in NADH was due to a reduction of mitochondrial function or due to the depletion of NAD$^+$ by PARP activation, CHO cells were co-exposed to MMS and specific PARP inhibitors. Specific PARP inhibitors, 3-aminobenzamide (3-AB; Sigma-Aldrich, St. Louis, Mo.)(10 mM) and 3,4-dihydro-5-[4-(1-piperidinyl) butoxy]-1(2H)-isoquinolinone (DPQ, Sigma-Aldrich, St. Louis, Mo.)(90 $\mu$M) were applied 1 to 2 hours prior to the MMS treatment and kept in the medium during MMS exposure until the cells were analyzed. 3-AB and DPQ almost completely blocked MMS-induced decreases in the amount of intracellular NAD(P)H in both EM9-V and EM9-XH5 cell lines (FIG. 3, Panels A and B). These results indicated that the decrease in intracellular NAD(P)H in CHO cells exposed to MMS for 4 hours was due to PARP activation through formation of single strand breaks.

EXAMPLE 4

NAD(P)H Reduction in the PARP-1$^{-/-}$ Cells

Figure 4:
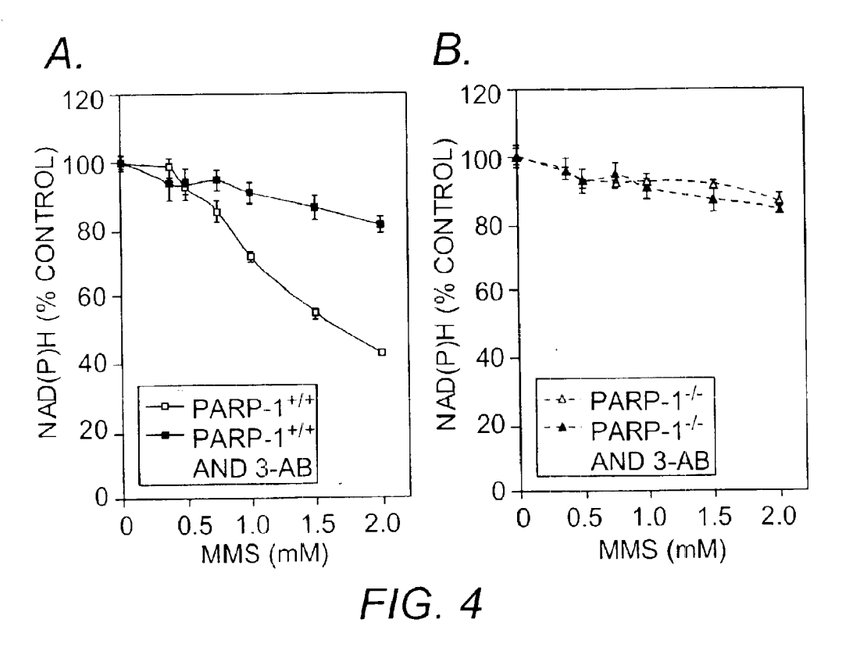
FIG. 4 shows the depletion of NAD(P)H in wild-type (PARP$^{+/+}$, Panel A) and PARP-1 knock-out (PARP$^{-/-}$, Panel B) fibroblast cells exposed to MMS for 4 hours in the absence or presence of 3-AB (10 mM). Results represent triplicate samples and the reproducibility was confirmed at least three times. Bars, standard deviation.

PARP-1$^{-/-}$ and PARP-1$^{+/+}$ cells were exposed to MMS to determine whether decreases in NAD(P)H were due to PARP activation. MMS reduced NAD(P)H in PARP-1$^{+/+}$ cells (FIG. 4, Panel A); whereas, PARP-1$^{-/-}$ cells were more resistant to the decrease in NAD(P)H (FIG. 4, Panel B). In addition, 3-AB protected PARP-1$^{+/+}$ cells from the reduction in NAD(P)H upon exposure to MMS. The slight decrease in NAD(P)H in PARP-1$^{-/-}$ cells may have been due to a reduction in mitochondrial function.

EXAMPLE 5

NAD(P)H Determination Assay Versus the Comet Assay

A direct comparison was conducted between the method of the invention measuring NAD(P)H and the Comet assay for the detection of single strand breaks. Slides for the Comet assay were prepared using well-known methods (Tennant, et al. (2001) *Mutat. Res.* 493:1–10). Briefly, slides were dipped into agarose and dried at 60° C. Low melting point agarose (0.5%) was prepared and held at 42° C. Cell suspensions (1×10$^4$ cells/10 $\mu$L) were mixed with 190 $\mu$L low melting point agarose. Ninety $\mu$L of this suspension was pipetted onto each of two slides and covered with a coverglass. Each slides was placed on ice for 5 minutes, the coverglass was removed, 90 $\mu$L of low melting point agarose was pipetted onto each slide, a coverglass was reapplied, and slides were returned to the ice. After 5 minutes, the coverglass was removed and the slides were placed in lysis buffer (pH 11) containing 2.5 M NaCl, 100 mM EDTA-2Na, 10 mM Tris, 1% Na Sarcosinate, 1% TRITON® X-100 and 10% dimethylsulfoxide for 20 minutes. Following lysis, the slides were placed in denaturation buffer (i.e., electrophoresis buffer; 300 mM NaOH, 1 mM EDTA, pH 13). Electrophoresis was carried out in a large horizontal unit (Fisher Biotech, Pittsburgh, Pa.) with a BIO-RAD® 1000 power Supply (BIO-RAD® Labs, Hercules, Calif.) for 20 minutes at 300 mV. Slides were removed and placed in a neutralizing buffer containing 0.4 M Tris, pH 7.5 for 15 minutes. Subsequently, the slides were placed in 95% ethanol for 5 minutes and allowed to air dry in a hood overnight.

Slides were stained using 35 $\mu$L of SYBR GREEN-1™ (MOLECULAR PROBES™, Eugene, Oreg.)(10× in Tris-EDTA buffer pH 8.0) and a coverglass was applied. Cells were viewed with a Leitz Orthoplan microscope with a 100 W Hg fluorescent light source and a Leitz 13 filter cube. A Dage CCD725 camera (Dage MTI, Michigan City, Iowa) was used to capture images. Fifty cells from each of two slides were analyzed by a independent scorer who had no knowledge of the treatment. The analysis was carried out using the KOMET™ 5.0 (Kinetic Imaging, UK) Comet analysis software. Data was collected for tail length and percentage of DNA in the tail. The endpoints were used to calculate tail moment by the KOMET™ 5.0 software using the formula: tail moment=tail length×percentage of DNA in the DNA/100. Simple linear regression (one-tailed) was performed after checking for homogeneity of variance using Cochran's C test and Bartlett's test. If a statistically significant positive slope was obtained, a one-tailed Dunnett's analysis was employed to compare each treatment mean to its relevant control. The culture was the unit of experimentation and in all tests, the $\alpha$ was set at 0.05. All tests were performed using the STAGPAPHICS™ Plus Version 5 statistical package.

Figure 5:
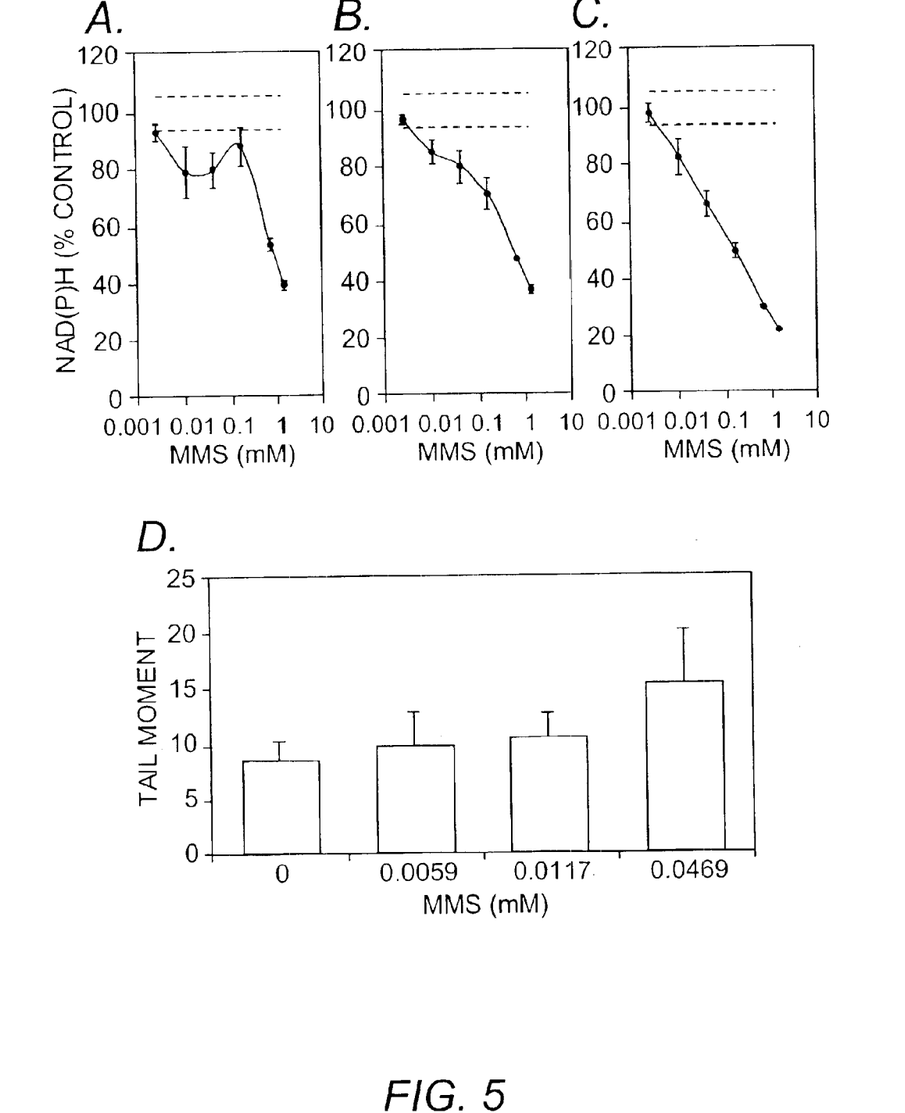
FIG. 5 shows a comparison of the cellular effects induced by MMS detected by NAD(P)H assay of the present invention and the Comet assay. Depletion of NAD(P)H in EM9-V cells exposed to MMS for 1 hour (Panel A), 2 hours (Panel B), and 4 hours (Panel C). Results represent triplicate samples and the reproducibility was confirmed at least three times. Bars, standard deviation. Panel D shows tail moments quantified by the Comet assay in EM9-V cells immediately after MMS treatment with 0, 0.0059, 0.0117, or 0.0469 mM for 1 hour. Results are the mean from triplicate samples. Bars, standard deviation.

Comparisons were conducted on XRCC1-deficient EM9-V cells exposed to MMS at concentrations as low as approximately 5 $\mu$M for 4 hours. The decrease in the amount of intracellular NAD(P)H was detected in cells exposed to MMS at concentrations as low as ~10 $\mu$M at 1, 2, and 4 hours (FIG. 5, Panels A, B, and C, respectively). Using the Comet assay, an increase in the amount of tail moment in EM9-V cells exposed to ~50 $\mu$M MMS was detected (FIG. 5, Panel D). These results indicate that the method provided herein is more sensitive than the Comet assay and is useful in assessing an imbalance of single strand breaks in cells.

EXAMPLE 6

NAD(P)H in Human Lymphoblastoid Cells Exposed to MMS

Figure 6:
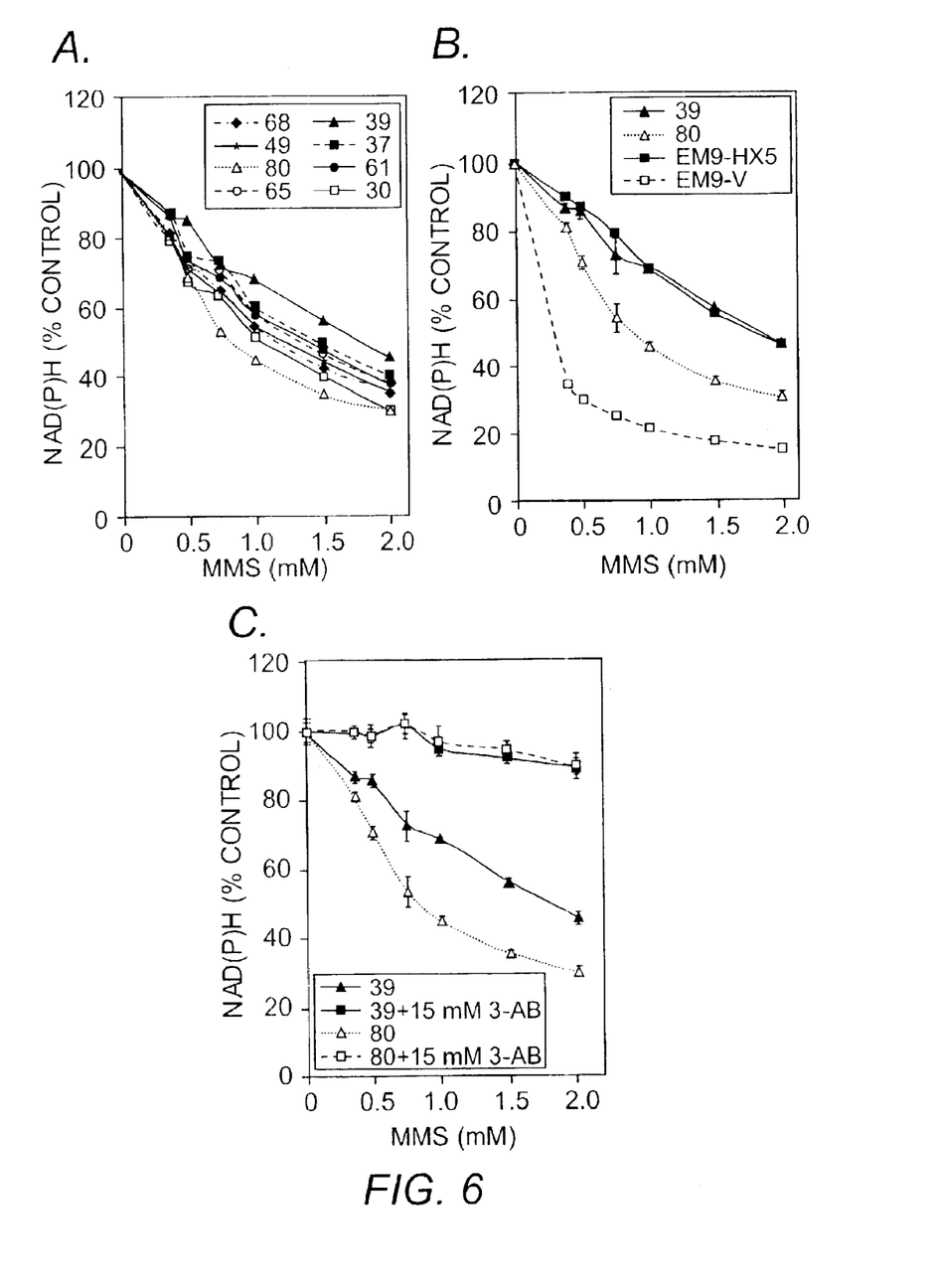
FIG. 6 shows results from an NAD(P)H assay of human lymphoblastoid cells established from eight healthy individuals. Panel A shows NAD(P)H depletion in lymphoblastoid cells (30: GM15030, 61: GM15061, 37: GM15237, 68: GM15268, 39: GM15339, 49: GM15349, 65: GM15365, and 80: GM15380) exposed to MMS for 4 hours. Panel B shows a comparison of NAD(P)H depletion between lymphoblastoid cells 39 and 80 and EM9-V and EM9-XH5 cells. Panel C shows NAD(P)H depletion of lymphoblastoid cells 39 and 80 exposed to MMS for 4 hours in the absence or presence of 3-AB (16 mM). Results represent triplicate samples and the reproducibility was confirmed at least three times. Bars, standard deviation.

Variations in the single strand break repair capacity in human lymphoblastoid cells established from eight different healthy individuals was determined. The method of detecting single strand breaks provided herein demonstrated a wide variation in the sensitivity to MMS in the lymphoblastoid cell lines (FIG. 6, Panel A). Data obtained from the most resistant cells (39: GM15339) and the most sensitive cells (80: GM15380) were compared to data from EM9-XH5 and EM9-V cells (FIG. 6, Panel B). The sensitivity of GM15339 was almost equivalent to that of XRCC1-proficient EM9-XH5 cells. In contrast, the GM15380 cell line was intermediate in sensitivity compared to the two isogenic EM9 cell lines. The decrease in NAD(P)H levels were significantly inhibited by co-incubation with PARP inhibitor (FIG. 6, Panel C). These results indicate that the method provided herein is useful for monitoring an imbalance of single strand break repair in population-based or clinical samples.

EXAMPLE 7

Detection of Intracellular NAD(P)H Using Either XTT or MTS

XTT[1] (2,3-bis[2-Methoxy-4-nitro-5-sulfophenyl]-2H-tetrazolium-5-carboxy-anilide inner salt) and MTS[2] (3-(4, 5-dimethylthiazol-2-yl)-5-(3-carboxynethoxyphenyl)-2-(4-sulfophenyl)-2H-tetrazolium, inner salt), water-soluble tetrazolium salts, were used to measure the amount of intracellular NAD(P)H through the reduction to a water-soluble formazan dye. EM9-V and XH5 cells were seeded into 96-well plates and were cultured in 100 $\mu$L of medium with fetal bovine serum and antibiotics as described (10,000 cells per well). After a 30-minute incubation, cells were treated with DMS (dimethylsulfate) at indicated concentrations and 1/10 volume of either XTT with an electron coupling agents such as phenazine methosulfate (Sigma) or MTS with phenazine methosulfate (Promega). Cells in each well were further cultured for up to 4 hours. Either XTT or MTS produced a water-soluble yellow-colored formazan dye and the absorbance was recorded in a 96-well plate reader at 450 nm with a 650 nm reference filter.

Figure 7:
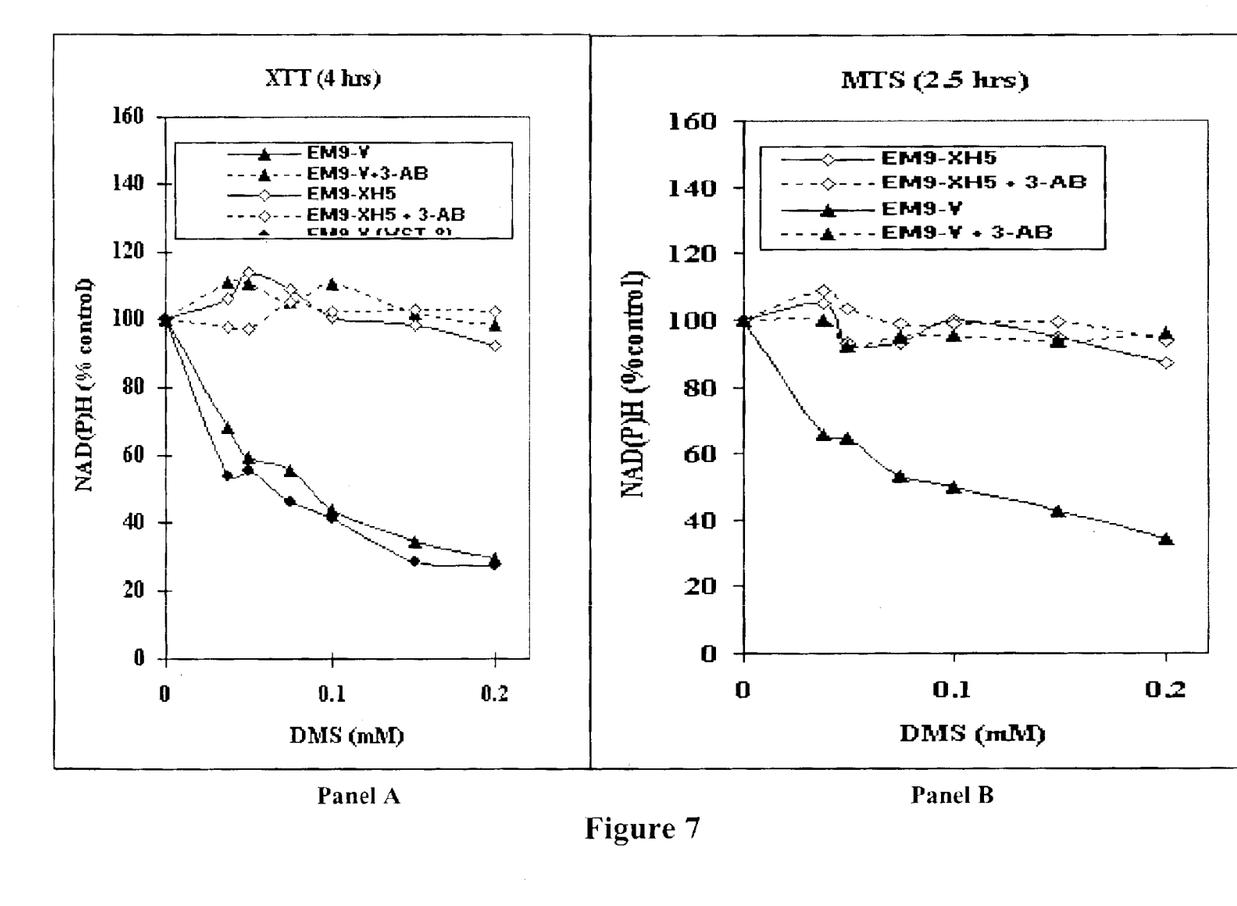
FIG. 7 shows dose-dependency of the depletion of NAD(P)H in EM9-V and EM9-XH5 exposed to DMS for 4 hours (using XTT; Panel A) and for 2.5 hours (using MTS; Panel B) in the absence or presence of PARP inhibitor, 3-aminobenzamide (3-AB) (10 mM). Results represent mean values from triplicate samples.

These cells were exposed to DMS at different concentrations for 2.5 or 4 hours. The intracellular NAD(P)H in EM9-V cell lines, but not in EM9-XH5 cells, was significantly reduced by treatment with DMS in a dose-dependent manner (FIG. 7, Panels A and B). In addition, CHO cells were co-exposed to DMS and PARP inhibitor, 3-aminobenzamide (10 mM) and were applied 1 to 2 hours prior to the DMS treatment and kept in the medium during DMS exposure until the cells were analyzed. 3-AB completely blocked DMS-induced decreases in the amount of intracellular NAD(P)H in both EM9-V cell lines (FIG. 7, Panels A and B). These results indicated that in addition to WST-8, both XTT and MTS can be utilize to monitor intercellular NAD(P)H levels in the living cells to monitor an imbalance of SSB repair. These data also indicate that any water-soluble tetrazolium salts to form water-soluble formazans (WST-1, -3, -4, and -8, XTT, and MST) can be utilized for quantitating intercellular NAD(P)H levels to monitor an accumulation of SSBs.

The foregoing examples are illustrative of the present invention, and are not to be construed as limiting thereof. The invention is described by the following claims, with equivalents of the claims to be included therein.

What is claimed is:

1. A method of detecting increased levels of DNA single strand breaks in a eukaryotic cell sample, comprising the steps of:
   (a) contacting a eukaryotic cell sample to a water-soluble tetrazolium salt under conditions in which said tetrazolium salt is converted to a formazan dye in said cell sample in the presence of NADH or NADPH; and then
   (b) detecting the presence of said formazan dye in said cell sample, with decreased levels of said formazan dye indicating increased levels of DNA single strand breaks in said eukaryotic cell sample;
   wherein a test compound is contacted to said cell sample before or during said contacting step (a), with increased levels of single stranded breaks indicating said test compound is genotoxic to said cell sample, and reduced levels of single stranded breaks indicating said test compound is protective to said cell sample.

2. The method according to claim 1, wherein said eukaryotic cell sample is a plant or animal cell sample.

3. The method according to claim 1, wherein said eukaryotic cell sample is a mammalian cell sample.

4. The method according to claim 1, wherein said eukaryotic cell sample is a live cell sample.

5. The method of claim 1, wherein said contacting step is carried out in an aqueous solution.

6. The method of claim 1, wherein said detecting step is carried out by detecting UV absorbance.

7. The method of claim 1, wherein said cell sample is subjected to oxidative stress before or during said contacting step, and wherein a test compound is contacted to said cell sample before or during said contacting step, with increased levels of single stranded breaks indicating said test compound exacerbates said oxidative stress, an reduced levels of single stranded breaks indicating said test compound is protective against said oxidative stress.

8. The method of claim 1, wherein said cell sample is collected from a plant or animal subject and contacted to a genotoxic compound, and wherein the amount of DNA single strand breaks in said cell sample is compared to that of a like cell sample which has not been contacted to said genotoxic compound.

9. The method of claim 1, wherein said cell sample is collected from a plant or animal subject and subjected to oxidative stress, and wherein the amount of DNA single strand breaks in said cell sample is compared to that of a like cell sample which has not been subjected to said oxidative stress.

10. The method of claim 1, wherein said water-soluble tetrazolium salt is a sulfonated tetrazolium salt.

11. The method of claim 1, wherein said water-soluble tetrazolium salt has the general formula:

wherein A, B and C are independently selected aryl or heteroaryl groups, which may be substituted or unsubstituted, with at least one of A, B. and C being substituted at least once with $SO_3^-$.

12. The method of claim 1, wherein said water-soluble tetrazolium salt has the general formula:

wherein $R^1$ and $R^2$ independently represent hydrogen or nitro, and M represents an alkali metal or an ammonium.

13. The method of claim 1, wherein said water-soluble tetrazolium salt has the general formula:

wherein $R^1$ and $R^2$ independently represent a hydrogen atom, nitro group, cyano group, carboxyl group, or a halogen atom; $R^3$ represents an alkyl group or an alkoxyl group; and M represents an alkali metal or an ammonium.

14. The method of claim 1, wherein said water-soluble tetrazolium salt selected from the group consisting of:

2-(2-methoxyl-4-nitrophenyl)-3-(4-nitrophenyl)-5-(2,4-disulfophenyl)-2H-tetrazolium, monosodium salt (WST-8);

4-[3-(4-iodophenyl)-2-(4-nitrophenyl)-2H-5-tetrazolio]1,3-benzene disulfonate (WST-1); and 2,3-bis[2-methoxy-4-nitro-5-sulfophenyl]-2H-tetrazolium-5-carboxanilide (XTT);

2-(4-Iodophenyl)-3-(2,4-dinitrophenyl)-5-(2,4-disulfophenyl)-2H-tetrazolium, sodium salt (WST-3);

2-Benzothiazolyl-3-(4-carboxy-2-methoxyphenyl)-5-[4-(2-sulfoethyl-carbamoyl)phenyl]-2H-tetrazolium (WST-4);

2,2'-Dibenzothiazolyl-5,5'-bis[4di(2-sulfoethyl) carbamoylphenyl]-3,3'-(3,3'-dimethoxy- 4,4'-biphenylene)ditetrazolium, disodium salt (WST-5).

15. The method of claim 1, wherein said water-soluble tetrazolium salt is (3-(4,5-dimethylthiazol-2-yl)-5-(3-carboxymethoxyphenyl)-2-(4-sulfophenyl)-2H-tetrazolium, inner salt (MTS).

16. The method of claim 1, wherein said water-soluble tetrazolium salt is 3-[4,5-dimethylthiazol-2yl]2,5-diphenyltetrazolium bromide (MTT).

17. The method of claim 1, wherein said cell sample comprises not more than 500,000 cells.

18. The method of claim 1, wherein said contacting and detecting steps are carried out within a total time not greater than four hours.

19. A method of detecting increased levels of DNA single strand breaks in a live eukaryotic cell sample, comprising the steps of:

(a) contacting a live eukaryotic cell sample comprising not more than 500,000 cells in an aqueous solution to a water-soluble tetrazolium salt under conditions in which said tetrazolium salt is converted to a water-soluble formazan dye in said cell sample in the presence of NADH or NADPH; and then (b) detecting the presence of said formazan dye in said cell sample, with decreased levels of said formazan dye indicating increased levels of DNA single strand breaks in said eukaryotic cell sample;

wherein said contacting and detecting steps are carried out within an time not greater than 4 hours;

wherein a test compound is contacted to said cell sample before or during said contacting step (a), with increased levels of single stranded breaks indicating said test compound is genotoxic to said cell sample, and reduced levels of single stranded breaks indicating said test compound is protective to said cell sample.

20. The method according to claim 19, wherein said eukaryotic cell sample is a plant or animal cell sample.

21. The method according to claim 19, wherein said eukaryotic cell sample is a mammalian cell sample.

22. The method of claim 19, wherein said water-soluble tetrazolium salt is 2-(2-methoxyl4nitrophenyl)-3-(4-nitrophenyl)-5-(2,4-disulfophenyl)-2H-tetrazolium, monosodium salt.

23. The method of claim 1, wherein said decreased level is as compared to a control.

24. The method of claim 19, wherein said decreased level is as compared to a control.

* * * * *